United States Patent [19]

Lesniak

[11] Patent Number: 5,719,395
[45] Date of Patent: Feb. 17, 1998

[54] COATING TOLERANT THERMOGRAPHY

[75] Inventor: Jon R. Lesniak, Madison, Wis.

[73] Assignee: Stress Photonics Inc., Madison, Wis.

[21] Appl. No.: 713,229

[22] Filed: Sep. 12, 1996

[51] Int. Cl.⁶ ........................................... G01N 25/72
[52] U.S. Cl. ................ 250/330; 250/341.6; 250/358.1
[58] Field of Search ........................... 250/330, 332, 250/341.6, 358.1, 359.1, 360.1

[56] References Cited

U.S. PATENT DOCUMENTS

| | | |
|---|---|---|
| 3,808,439 | 4/1974 | Renius ........................... 250/341.6 |
| 4,172,382 | 10/1979 | Murphy et al. . |
| 4,184,768 | 1/1980 | Murphy et al. . |
| 4,468,136 | 8/1984 | Murphy et al. . |
| 4,589,783 | 5/1986 | Thomas et al. . |
| 4,647,220 | 3/1987 | Adams et al. ................... 250/330 X |
| 4,724,482 | 2/1988 | Duvent . |
| 4,798,477 | 1/1989 | Mountain . |
| 4,854,724 | 8/1989 | Adams et al. . |
| 4,866,279 | 9/1989 | Leavens et al. . |
| 4,874,251 | 10/1989 | Thomas et al. . |
| 4,878,116 | 10/1989 | Thomas . |
| 4,886,370 | 12/1989 | Koshihara et al. . |
| 4,968,144 | 11/1990 | Thomas et al. . |
| 4,983,836 | 1/1991 | Matoba et al. . |
| 4,996,426 | 2/1991 | Cielo et al. ................... 250/359.1 X |
| 5,012,112 | 4/1991 | Flint et al. . |
| 5,051,591 | 9/1991 | Trotta et al. . |
| 5,089,700 | 2/1992 | Sapia et al. ................... 250/330 |
| 5,111,048 | 5/1992 | Devitt et al. . |
| 5,118,945 | 6/1992 | Winschuh et al. . |
| 5,201,582 | 4/1993 | Lesniak . |
| 5,208,766 | 5/1993 | Chang et al. . |
| 5,240,329 | 8/1993 | Zinkosky . |
| 5,292,195 | 3/1994 | Crisman, Jr. . |
| 5,344,236 | 9/1994 | Fishman . |
| 5,376,793 | 12/1994 | Lesniak . |
| 5,446,283 | 8/1995 | Dautriche . |
| 5,451,785 | 9/1995 | Faris . |
| 5,532,488 | 7/1996 | Ishibashi et al. . |

OTHER PUBLICATIONS

Elliot et al., "Thermographic Imaging of Cracks in Thin Metal Sheets", SPIE, vol. 1682, Thermosense XIV, pp. 162-170.

Farvo et al., "Inversion of pulsed thermal-wave images for defect sizing and shape recovery" SPIE, vol. 1682, Thermosense XIV, pp. 178-181.

Spicer et al., "Source patterning in time-resolved infrared radiometry (TRIR) of composite structures ", SPIE, vol. 1682, Thermosense XIV, pp. 248-257.

Primary Examiner—Edward J. Glick
Attorney, Agent, or Firm—Lathrop & Clark

[57] ABSTRACT

Cracks in bridges or other structures are detected by applying a thermal gradient to the test structure in a selected region so heat flows from left to right. A first image of the thermal gradient with heat flowing from left to right is taken and stored for further processing. Next a thermal gradient is applied so heat flows from right to left through the selected region. A second thermal image is taken and stored of the heat flowing from right to left. An image taken before a thermal gradient is applied is subtracted from the first and second images to remove thermal reflection and non-induced gradients from the stored images. Each differentiated image is then normalized by dividing each pixel of the differentiated image by the total photon flux from the undifferentiated image. The second image is than subtracted from the first image producing a third image which highlights features which produce thermal gradients of opposite signs. Paint chips and paint drips and other variations in surface emissivity which can produce the appearance of a thermal gradient have the same apparent gradient when heat is applied from either side. Thus the technique of utilizing two temperature gradient images where the gradient is applied from opposite sides uniquely highlights real defects.

20 Claims, 6 Drawing Sheets

COATING TOLERANT THERMOGRAPHY

LICENSE RIGHTS

The U.S. Government has a paid-up license in this invention and the right in limited circumstances to require the patent owner to license others on reasonable terms as provided for by the terms of Contract No. DTRS 57-96-C-0068 awarded by the Department of Transportation Federal Highway Agency.

FIELD OF THE INVENTION

The present invention relates to methods and apparatus for performing nondestructive testing in general and methods and apparatus for detecting material flaws with thermal diffusion in particular.

BACKGROUND OF THE INVENTION

The Federal Interstate Highway System is one of the engineering marvels of the twentieth century. Recently questions have arisen concerning the adequacy of the maintenance which is a performed on the existing Interstate System. Questions have arisen about whether budget constraints and parochial interests in local highway projects have resulted in neglect of critical maintenance tasks such as the inspection and painting of the nation's many steel bridges. Concerns have focused on whether existing steel structures are suffering from stress cracking to a degree which would jeopardize safety.

Many methods have been devised for the non destructive evaluation of structures. X-ray examination has been found useful for detecting in-depth density variations; yet x-ray examination requires access to both sides of a specimen. Further, x-rays can involve the use of hazardous materials, and are not always successful in detecting cracks which do not produce density variations.

Dye-penetrant, ultrasound, and eddy-currents have been used to detect weld flaws, and structural stress and corrosion cracks. These methods, however, can be labor intensive, require physical contact with the test object, and often require special preparation of the material's surface.

A belief that thermal imaging (thermography) would lead to more cost-effective material flaw detection has led to a number of techniques employing thermal radiation and the test specimen's reaction to the thermal radiation to detect material flaws.

One such technique employs a high-power, pulsed thermal wave, which propagates into the material as a planar wave of thermal energy. When the thermal wave reaches a defect within the depth of the object being tested, that portion of the wave which encounters the defect is reflected with the amount of the reflected energy dependant on the nature of the discontinuity. The reflected wave is detectable at the surface by thermal imaging. This method, while being useful in some circumstances, requires high-power flash lamps and does not detect flaws which are normal to the surface of the object being tested.

Another thermal imaging process for detecting material defects, particularly stress cracks, employs a laser which performs a raster scan of a test object while the test object is being thermally imaged. This method requires a laser of relatively high power and detects surface cracks by their greater absorption of energy. This method can be somewhat sensitive to the angle of incidence. Further, the decay of the transient thermal response of the crack must be carefully analyzed to distinguish surface blemishes from cracks having significant depth. This method also requires a relatively clean surface, free of surface film and paint.

Another known technique, sometimes referred to as the "mirage effect," employs a heating laser which generates an output which is intensity modulated to provide a periodic optical signal used to periodically heat a point on the surface of an object. The optical beam from a probe laser passes parallel to the surface of the object through the heated zone. This probe beam is deflected from a normal path due to density variations in the air above the surface of the sample caused by the heating of the surface by the probe laser. The deflection of the probe laser from its nominal path indicates the presence of surface or sub-surface cracks, flaws, or voids in the object being tested. This type of apparatus requires a scan head located relatively close to the surface of the object being tested to recover the output of the probe beam.

One method for detecting flaws in welds involves heating the weld with an infrared source and observing the heated weld with an infrared camera to detect the thermal response of the weld, which may be indicative of weld flaws.

In principle, thermographic testing involves exposure of the analyzed surface to even heating. Variations in the thermoconductivity of the features below the surface then allow heat to flow away from the surface more rapidly in some places than others, establishing temperature gradients along the surface that provide an indication of the subsurface features in an object.

One type of apparatus which employs the thermographic technique has a linear heat source which is passed in spaced relation over the surface in front of a row of detectors. The heat source establishes a temperature gradient on the surface being tested. The sensors monitor the temperature gradient for variations which indicate surface defects. This process suffers from requiring the heat source and the detector to be moved closely over the surface of the object to be tested.

One variation on this process of using lateral heat flow to detect sub-surface flaws involves using a linear heating source, such as a laser projected through a cylindrical lens and an infrared scanner which views a line of material spaced from, and offset from, the linear heat source. Variations in the temperature gradient between the heat source and the infrared scanned line indicate the presence of cracks and material defects in the tested sample. This system is experimental in nature and requires a relatively intense heat source, with a change of temperature gradients in the material which can amount to several degrees or more.

Overall thermal diffusion techniques would appear to offer a cost effective technique for detecting stress cracks in steel structures. However the effectiveness of the technique is limited by the need to clean the surface being examined so that paint chips, paint drips, bird droppings, etcetera, are not confused with material defects. A requirement that the surface be clean in order that thermal diffusion techniques can be employed limits their utility for rapid survey of structures in the field. Many thousands of steel structures are in need of examination and often it is desirable to repeat the examination over time to determine if flaws detected are stable or are getting worse with time.

Steel is a ductile material and to the extent cracks present in structures are not growing over time the cracks may not present a threat to the structural integrity of a structure. If the cracks continue to grow, however, this indicates that the structure is experiencing high stress and/or brittle failure where the cracks are present. Because of the many structures which are in need of inspection and because the most cost effective way of detecting structures most in need of repair is frequent monitoring, a technique for nondestructive evaluation of these structures which is easily transported and does not require expensive preparation or cleaning of the surfaces to be examined is required.

SUMMARY OF THE INVENTION

The method of this invention employs a thermal gradient to detect cracks in bridge structures. The thermal gradient is applied so heat flows from left to right through a region being examined for cracks. A first thermal image of the heat flowing from left to right is taken and stored for further processing. Next a thermal gradient is applied so heat flows from right to left through the region being examined for cracks. A second thermal image is taken and stored of the heat flowing from right to left. An image taken before a thermal gradient is applied is subtracted from the first and second images to remove thermal reflection and non-induced gradients from the stored images. Each stored image is then digitally processed to produce an image of the differentiated thermal gradient. Each differentiated image is then normalized by dividing each pixel of the differentiated image by the total photon flux from the undifferentiated image. The second image is then subtracted from the first image producing a third image which highlights features which produce thermal gradients of opposite signs. Paint chips and paint drips and other variations in surface emissivity which can produce the appearance of a thermal gradient have the same apparent gradient when heat is applied from either side. Thus the technique of utilizing two temperature gradient images where the gradient is applied from opposite sides uniquely highlights real defects.

The images of the differentiated temperature gradient can be produced with a direct digital technique where an infrared sensor array produces an image which is digitally processed to obtain the differentiated image of the gradient.

A second, or analog, technique for obtaining a differentiated image of the gradient is to oscillate the image projected on the infrared sensor array along the direction of the gradient and perform an autocorrelation on the image which directly provides a differentiated image of the gradients.

It is an object of the present invention to provide a method of nondestructive evaluation which will not show changes in surface emissivity as defects.

It is a further object of the present invention to provide a method and apparatus for in-field inspection of steel and concrete structures.

It is another object of the present invention to provide a thermal illumination source for nondestructive testing which efficiently transmits thermal energy to a structure.

It is a further object of the present invention to provide a method of detecting stress cracks in existing bridge structures.

It is a yet further object of the present invention to provide a method of detecting flaws in a structure which does not require extensive preparation of the surface to be imaged.

Further objects, features and advantages of the invention will be apparent from the following detailed description when taken in conjunction with the accompanying drawings.

DESCRIPTION OF THE PREFERRED EMBODIMENT

Figure 1:
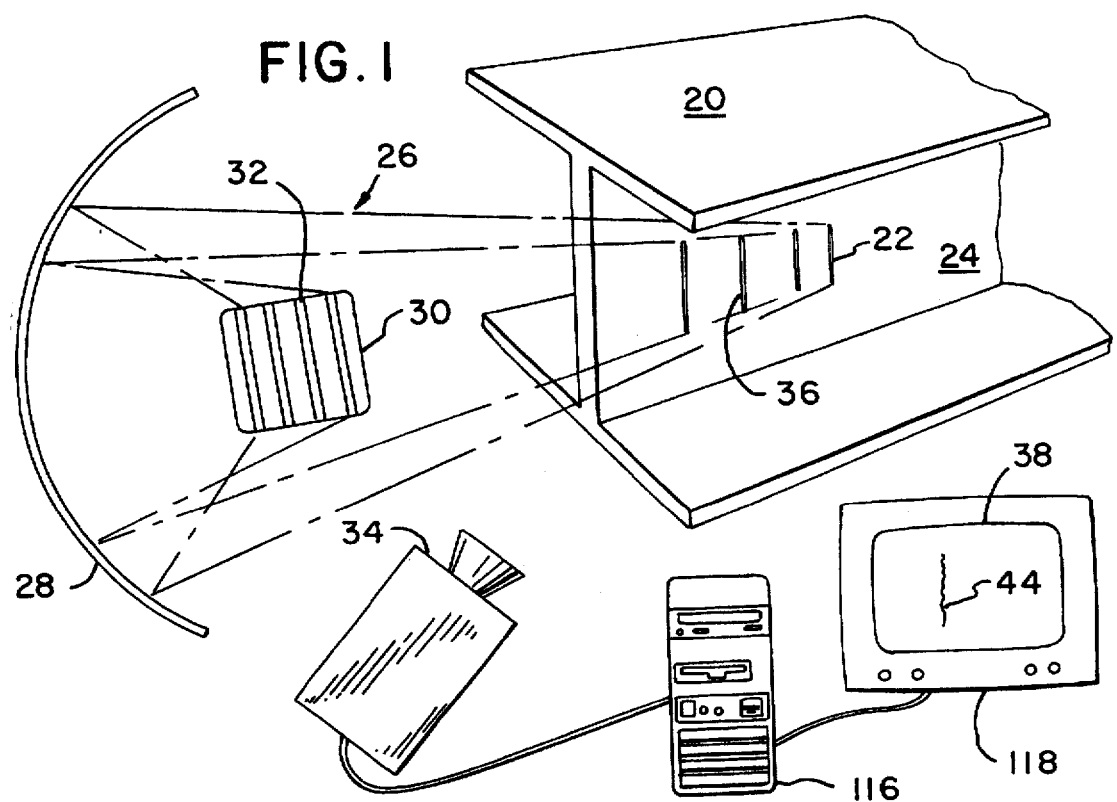
FIG. 1 is a pictorial isometric view of the apparatus for performing the nondestructive evaluation technique of this invention.

Referring more particularly to FIGS. 1–18 wherein like numbers refer to similar parts a structural member 20 of a bridge is shown in FIG. 1. A pattern of thermal radiation 22 is projected onto the surface 24 of the structural member 20 by a thermal projector 26. The thermal projector 26 utilizes an infrared optical element comprised of a simple spherical mirror 28 to project the image 22 of a heater 30 onto the structure 20. The heater 30 has a series of heating Nicrome wires 32 arrayed parallel to each other. The wires comprise an array of selectably energizable elements. Pseudo motion of the projected radiation patterns 22 can be effected by switching adjacent wires 32 on and off like marquee lights. A thermal imaging camera 34 images the structure 20. The image obtained by the camera 34 may or may not contain a portion of the structure on which elements 36 of the thermal pattern 22 are visible. The image obtained by the camera 34 covers a region where a thermal gradient has been induced by the radiation pattern 22.

Figure 5:
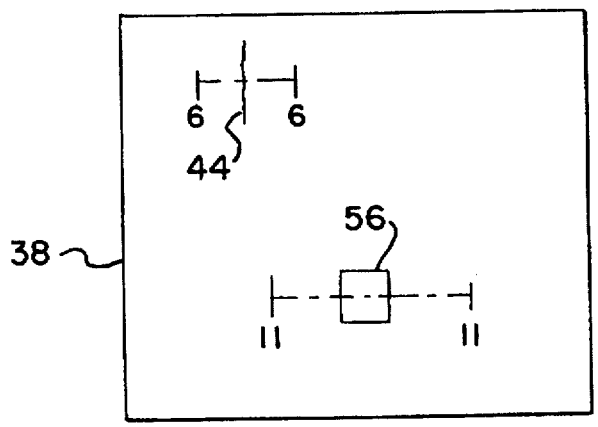
FIG. 5 is a schematic plan view of a region of a steel structure which contains a stress crack and a paint chip.
Figure 6:
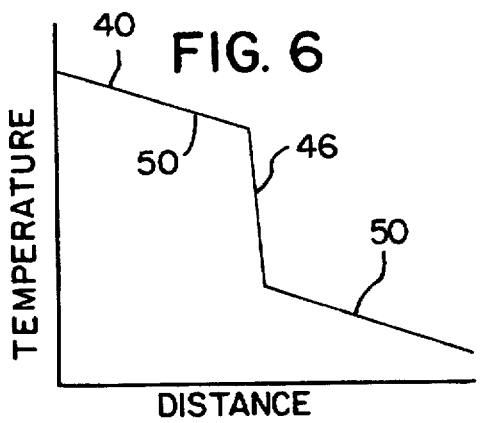
FIG. 6 is a plot of the temperature across the stress crack in FIG. 5 taken along line 6—6 when heat is applied to the structure of FIG. 5 to the right of the stress crack.
Figure 7:
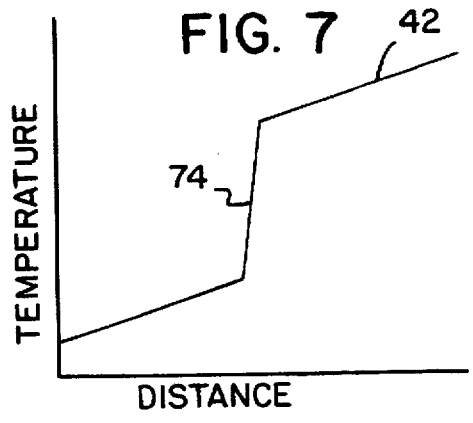
FIG. 7 is a plot of the temperature across the stress crack in FIG. 5 taken along line 6—6 when heat is applied to the structure of FIG. 5 to the left of the stress crack.

For each region 38 of the structure which is inspected for stress cracks, as shown in FIG. 5, an image of the region 38 is obtained where a thermal gradient has been induced from the left and a second image is obtained where a thermal gradient has been induced from the right. A thermal gradient which has been imposed on a structure is highly effective at detecting fractures in the material. As heat flows along the surface of a structure if a crack is present and is substantially normal to the direction of heat flow, the crack will impede the flow of heat along the surface of the structure. Even an extremely narrow crack, which is visually difficult to detect, presents a molecular discontinuity which impedes the flow of thermal energy by conduction. The result is that there is a significant drop in the temperature of the surface viewed by the camera 34 on the side of the crack away from the source of heating. FIG. 6 shows a plot line 40 of the surface temperature versus distance along the line 6—6 of the region 38 shown in FIG. 5 when heat is applied to the left of the region 38 to create a left-to-right thermal gradient. FIG. 7 shows a view similar to that shown in FIG. 6 with the difference that heat is applied to the right of the region 38 and thus creates a right-to-left thermal gradient—the temperature being shown by a plot line 42.

Figure 8:
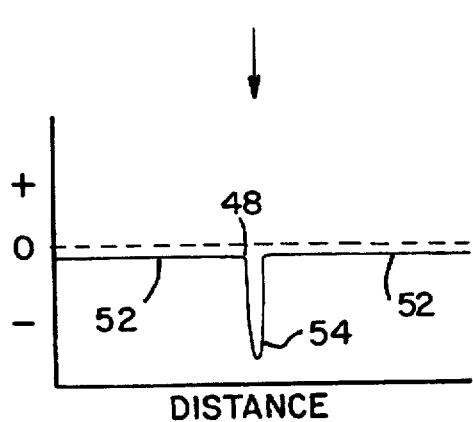
FIG. 8 is a plot of the derivative of the thermal gradient of FIG. 6.

The line 40 slopes to the right and thus has a negative slope. Where the line 40 crosses the crack 44, as illustrated in FIG. 5, a steep change in temperature 46 is shown on the plot line 40. This steep change in temperature is a decrease in temperature and thus represents a large negative temperature gradient. FIG. 8 is plot 48 of the derivative of the line 40 of FIG. 6 and is thus a plot of the change in temperature gradient across the crack 44. Although the line 40 in FIG. 6 is shown as not smooth the data as actually collected by the camera 34 smooths the abrupt change in temperature 46 which results in a differentiable curve. The constant slope portions 50 of the plot 40 when differentiated result in a small negative constant value 52, and the abrupt negative portion 46 of the plot 40 results in a large negative change 54 in gradient. An image constructed from multiple differentiated lines taken parallel to the direction of heat flow will show clearly stress fracture cracks such as crack 44. However such an image will also show discontinuities in surface emittance such as caused by a paint chip or a paint drip or other surface blemish.

Figure 11:
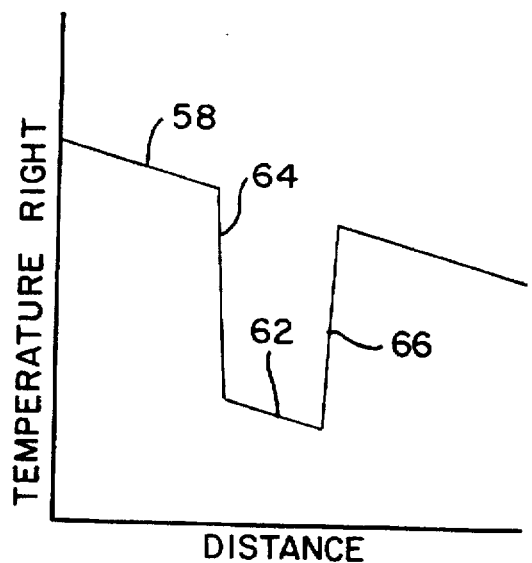
FIG. 11 is a plot of the temperature across the paint chip in FIG. 5 taken along line 11—11 when heat is applied to the structure of FIG. 5 to the right of the paint chip.
Figure 12:
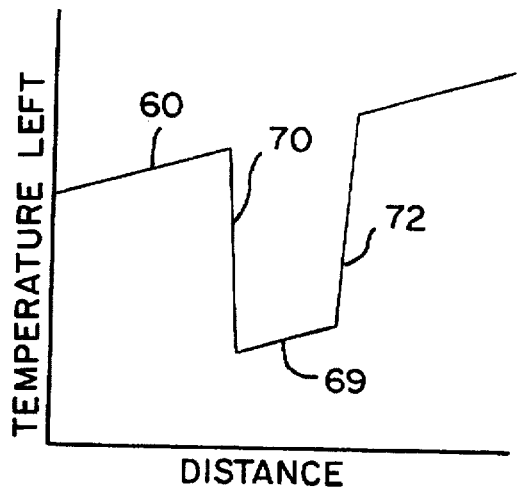
FIG. 12 is a plot of the temperature across the paint chip in FIG. 5 taken along line 11—11 when heat is applied to the structure of FIG. 5 to the left of the paint chip.

FIG. 11 illustrates the temperature of the region 38 taken along line 11—11 across the paint chip 56 by a plot line 58. The paint chip 56 is illustrated in FIGS. 11 and 12 as having an emittance significantly lower than the surrounding surface, however the following explanation also applies where the discontinuity is of a higher emittance than the surrounding material.

An abrupt change in surface emittance which produces an apparent abrupt change in surface temperature can be distinguished from an abrupt change in temperature which signifies a stress crack by comparing two images taken when thermal gradients of opposite sign are present. This is the key phenomenon. A stress crack produces a buildup of heat on the side of the crack facing the source of heating. Thus the buildup occurs on the left of the crack if heating is from the left, and the buildup occurs on the right of the crack if heating is from the right. Where no heat is built up but a surface change in emissivity causes an apparent change in temperature the sign of the change is the same whether heated from the left or the right. The temperature profile plots 58 of FIG. 11 and the profile plot 60 of FIG. 12 illustrates this principal.

Assume that the region 38 shows a portion of structure 20 which is coated with paint. The paint chip 56 illustrates a portion of the structure where the paint has chipped away revealing a surface with significantly lower emittance. (If the surface under the chipped paint has substantially the same emittance no temperature gradient effect is produced and the chip does not significantly affect the imaged gradient.) FIG. 11 illustrates a left-to-right gradient where the surface temperature of the chip 56 is represented by a sharp step 62 in the plot 58. Because the emittance of the chip 56 is less than the emittance of the machipped paint, on the side of the chip facing the temperature source the change in emittance produces a sharp step down 64 and a sharp step up 66 on the side away from the temperature source. FIG. 12 illustrates that when the temperature gradient is reversed and heat is supplied from the right, the plot 60 of temperature versus distance has a positive slope. However, the change in apparent temperature caused by the paint chip 64 has the same direction. As measured from the left the apparent temperature drops, as shown by sharp step 69 which has step-down segment 70 and which is followed by a sharp step up 72 on the other side of the paint chip. Thus although the step 62 of FIG. 11 is not identical to the step 69 of FIG. 12 the shape and magnitude are nearly the same. On the other hand the real temperature change produced by the stress crack 44 produces a step 74 in the plot 42 shown in FIG. 7 which is opposite in sign to the step 46 shown in FIG. 6. Thus the sign of the temperature change produced by the stress crack 44 changes depending on whether the thermal gradient is induced from the left or the right.

Figure 2:
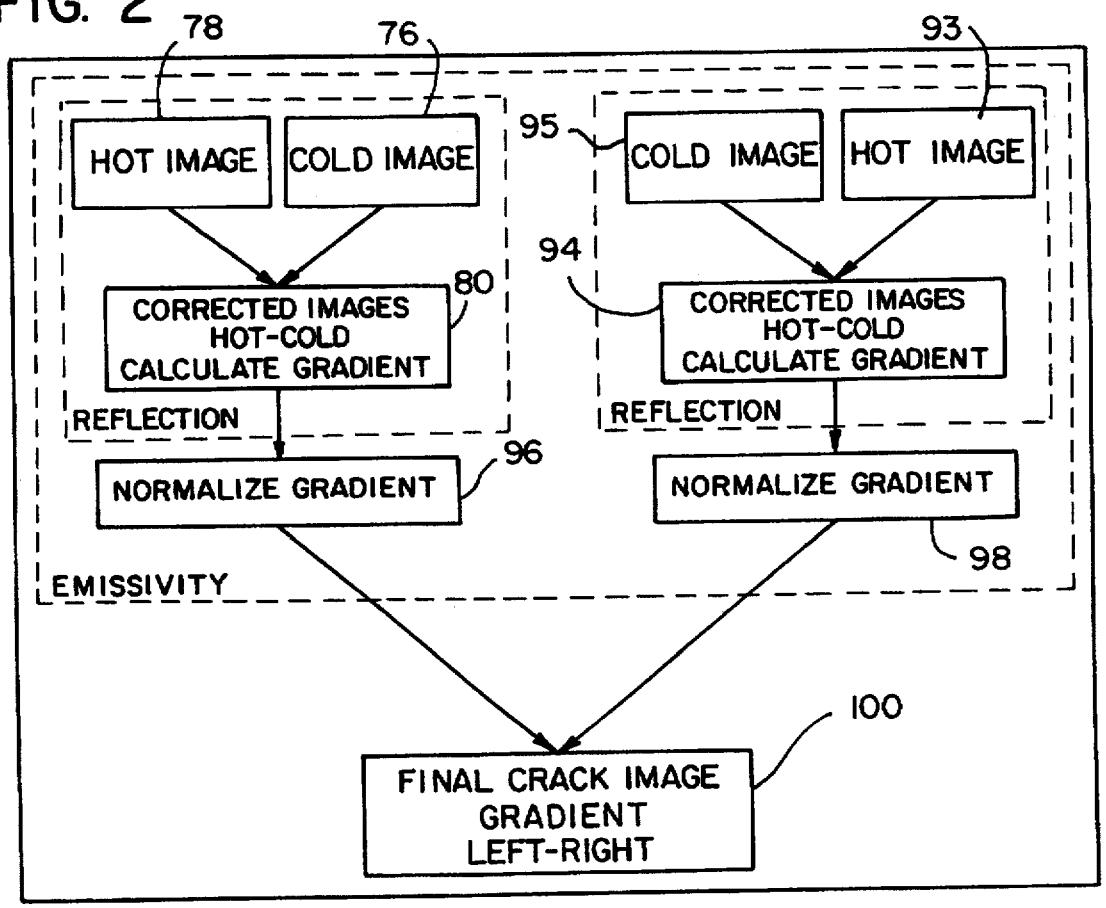
FIG. 2 is a flow diagram of the method of detecting stress cracks of this invention.
Figure 17:
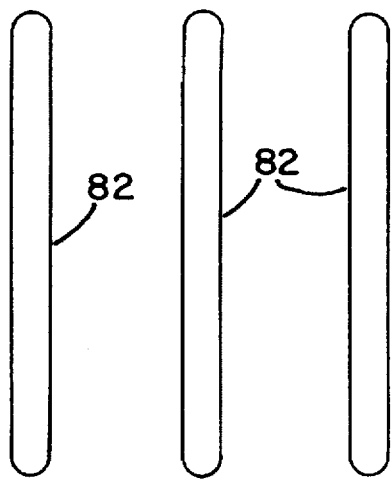
FIG. 17 is a plan view of a thermal pattern for performing the nondestructive evaluation technique of FIG. 1.
Figure 18:
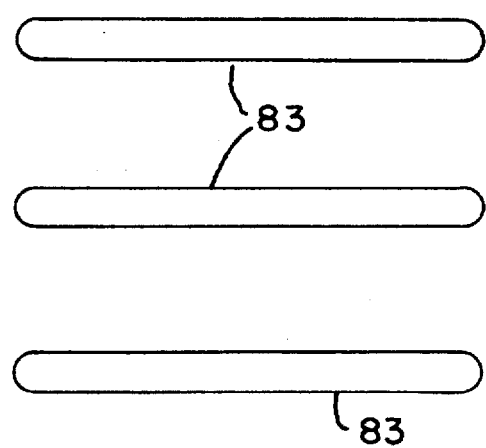
FIG. 18 is a schematic plan view of a series of non moving thermal patterns for performing the nondestructive evaluation technique of FIG. 1.

To use this principal to produce a useful image showing only real stress cracks in a structure 20, a number of discrete steps must be performed on the images obtained. FIG. 2 shows a block diagram of the steps necessary. First a thermal image of a selected region 38 is taken, indicated by step 76 labeled Cold Image. Next heat is applied to the left side of the selected region 38 to create a thermal gradient from left to right. Sufficient time after the application of the heat is allowed to establish a gradient across the selected region 38. This time may range from about five to ten seconds to about one minute. A thermal image is taken of the selected region 38 with the induced left-to-right gradient. This step 78 is labeled the Hot Image. The Cold Image is subtracted from the Hot Image, as shown as step 80 in FIG. 2. The resultant image has temperature artifacts from reflecting and preexisting thermal gradients removed. The corrected image formed in step 80 is then differentiated along a direction parallel to the propagation of heat through the selected region. When the heat is applied by fixed or slowly moving horizontal lines 82 as shown in FIG. 17, or vertical lines 83, the direction of integration will be normal to the lines 82, 83.

An image which is differentiated along the direction of heat propagation can be obtained by two methods, a digital operation on the gradient image as obtained in step 80 or by means of a lock-in operation performed on an image which is oscillated.

Figure 3:
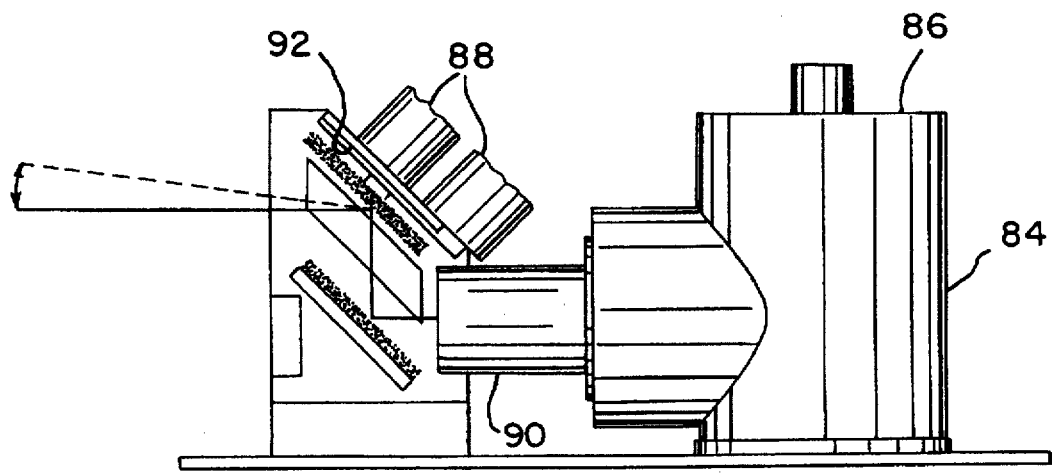
FIG. 3 is a side elevational view of an alternative apparatus for performing the nondestructive evaluation of this invention which employs an oscillating mirror to derive a derivative of the thermal gradient.

FIG. 3 shows an apparatus for obtaining an analog differentiated image. A thermal camera 84, which has an outer cryogenic container 86, views the selected region 38 through an infrared optical element 90. The line of sight is oscillated by actuators 88 which drive a mirror 92 so that the viewed image oscillates along the direction of the thermal gradient. The camera takes 434 images a second while the actuators 88 cause the image to oscillate at ten Hertz. The magnitude of the oscillation is from a fraction of a pixel wide to about one pixel wide. An autocorrelation at ten Hertz is performed on the collected images and those pixels which are located at steep changes in the thermal gradient produce a highly correlated value whereas pixels located with a small gradient produce a small or no correlated signal. The correlation algorithm produces a phase and magnitude of the correlated signal. The phase of the signal can be interpreted to obtain the sign of the change in gradient. For further discussion of lock-in algorithms see my earlier U.S. Pat. Nos. 5,201,582 and 5,376,793 which are incorporated herein by reference.

Referring to the block diagram of FIG. 2 a second image is obtained in step 94 similar to the differentiated image obtained in step 80 except that the image is taken as heat flows from the right to left through the selected region 38. As for the first image, a cold image is taken in step 95 and subtracted from a hot image of the thermal gradient taken in step 93. Before the first and second images obtained in step 80 and step 94 can be subtracted each image must be normalized to remove the effects of differing temperatures within the selected region when the first, as opposed to the second image, is taken.

Normalization is accomplished in steps 96 and 98 by dividing each pixel of the differentiated image by the total radiance of each pixel in the corrected image. This normalization removes the effects of the variations in temperature of the selected region 38 between when the first image and the second image are taken. Normalization allows a subtraction of the images which eliminates features which do not change sign with the direction of heat flow.

The following mathematical development provides an explanation of why division of the differentiated image at each pixel by the total radiance of the undifferentiated pixel of the corrected images, produces an image where differences in temperature are normalized. Differences in emissivity between the images is removed by the operation of subtracting the normalized images.

A body's ability to radiate photons is a function of temperature and emissivity. $I(x)=f(T(x))e(x)$, x being the position on the structure. To simplify, the photon emission for two heating cycles can be represented by $$I_L(x)=f(x)e(x)$$

$$I_R(x)=g(x)e(x)$$

Where f(x) and g(x) are the corrected photon emissions of black body, and $I_L(x)$, are $I_R(x)$ are the actual grey body emissions.

The spatial derivatives of these functions are by the product rule:

$$I_L'(x)=f'(x)e(x)+f(x)e'(x)$$

$$I_R'(x)=g'(x)e(x)+g(x)e'(x)$$

If I normalize each image by the absolute image f(x)e(x) or g(x)e(x) respectively, we get:

$$\bar{I}_L(x) = \frac{f'(x)}{f(x)} + \frac{e'(x)}{e(x)}$$

$$\bar{I}_R = \frac{g'(x)}{g(x)} + \frac{e'(x)}{e(x)}$$

The difference of these images results in:

$$\bar{I}_L(x) - \bar{I}_R(x) = \left(\frac{f'(x)}{f(x)} + \frac{e'(x)}{e(x)}\right) - \left(\frac{g'(x)}{g(x)} + \frac{e'(x)}{e(x)}\right)$$

$$= \left(\frac{f'(x)}{f(x)} - \frac{g'(x)}{g(x)}\right)$$

This implies that e'(x) has no influence on the image. The normalized thermal functions will change sign for real cracks and therefore not cancel.

Following the normalization of the first and second images in steps 96 and 98 the first and second images are subtracted in step 100 to form a final image which highlights cracks within a structure such as the bridge structure 20 shown in FIG. 1.

Figure 9:
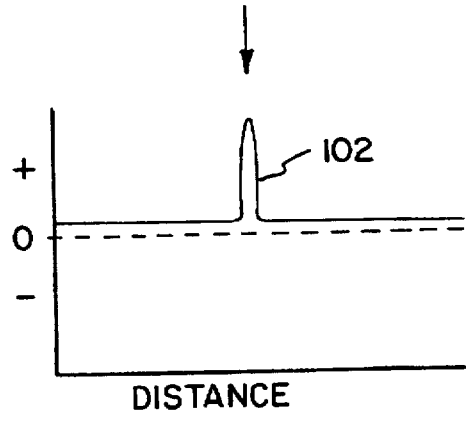
FIG. 9 is a plot of the derivative of the thermal gradient of FIG. 7.
Figure 10:
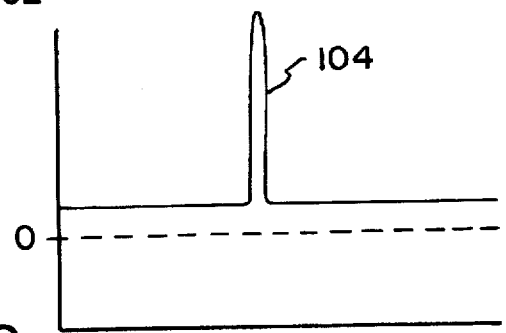
FIG. 10 is a graphical subtraction of FIG. 8 from FIG. 9.

The plot 48 in FIG. 8 represents the corrected differentiated image obtained in step 96 of FIG. 2. The plot 102 shown in FIG. 9 represents the differentiated image obtained in step 98 of FIG. 2 and more particularly represents the derivative of the gradient i.e. slope, of the plot 42 in FIG. 7 of the temperature along lines 6—6 across the stress crack 44. Subtraction of the plot 48 of FIG. 8 from the plot 102 of FIG. 9 produces a resulting plot 104 which highlights the crack 44 which produces a gradient change of opposite sign as heat flows from left to right and right to left.

Figure 13:
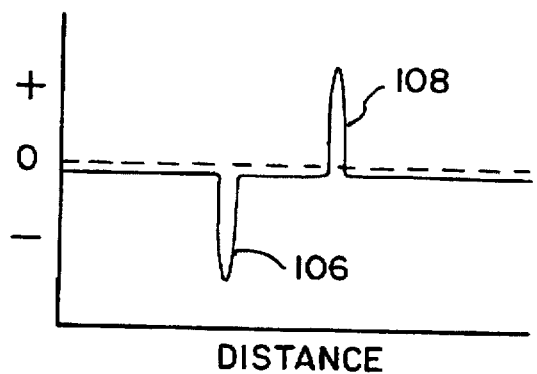
FIG. 13 is a plot of the derivative of the thermal gradient of FIG. 11.
Figure 14:
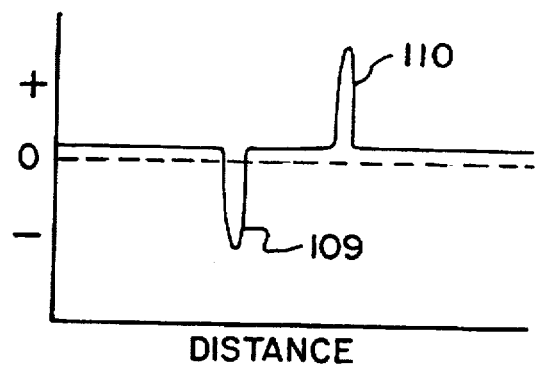
FIG. 14 is a plot of the derivative of the thermal gradient of FIG. 12.
Figure 15:
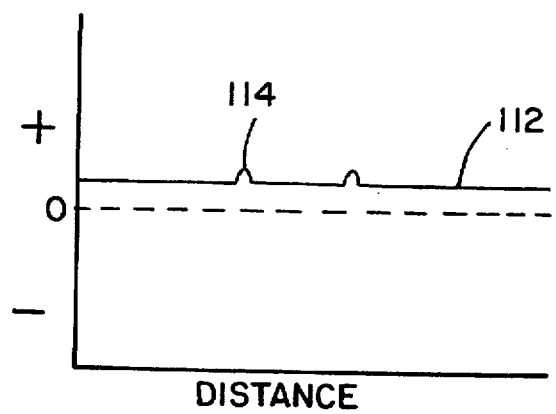
FIG. 15 is a graphical subtraction of FIG. 13 from FIG. 14.

A paint chip 56 produces a left to right gradient plot 58 shown in FIG. 11 and a right to left gradient plot 60 shown in FIG. 12, where the sign of the abrupt changes in radiance caused by a change in emissivity is the same in both plots and the images they represent. FIG. 13 shows the normalized differential of the thermal gradient plots of FIG. 11, and FIG. 14 shows the normalized differential of the thermal gradient plot of FIG. 12. FIG. 13 shows a negative peak 106 which corresponds to the negative slope 64 caused by the difference in emittance between the painted and unpainted surface of the selected area 38 of FIG. 5. Similarly positive peak 108 corresponds to the positive slope 66 caused by the transitions from the unpainted chip to the painted surface. Referring to FIG. 14 a negative peak 109 corresponds to the negative slope 70 and positive peak 110 corresponds to the positive slope 72 of FIG. 12. When the gradient differentials of FIG. 13 and 14 are subtracted the resultant plot 112 has no resultant peak or only a weak peak 114 which can be removed from the final image with a bias.

FIG. 1 shows a typical apparatus for performing the nondestructive evaluation described herein. A projector 26 projects infrared images 22 onto the surface 24 of a structure 20. An infrared camera 34 images the surface 24. Images are selected for each region 38 where heat is flowing in opposite directions through the region 38 and are processed by a computer or processor 116. The result is shown on a display 118 such as a computer monitor.

In order to detect cracks in all directions heat must be caused to flow in multiple direction, for example in four cardinal directions. Thus vertical thermal bars 82 will be alternated with horizontal thermal bars 83. If the thermal bars 82, 83 represent projected patterns which move slowly over the surface of a structure along lines perpendicular to the vertical or horizontal direction defined by the bars, a selected area on the structure will be heated from first one side than the opposite side as the bars 82, 83 pass over the selected area. In some circumstances the bars 82, 83 may be heating elements in actual contact with the structure which are discretely moved or continuously dragged over the surface being evaluated.

Figure 16:
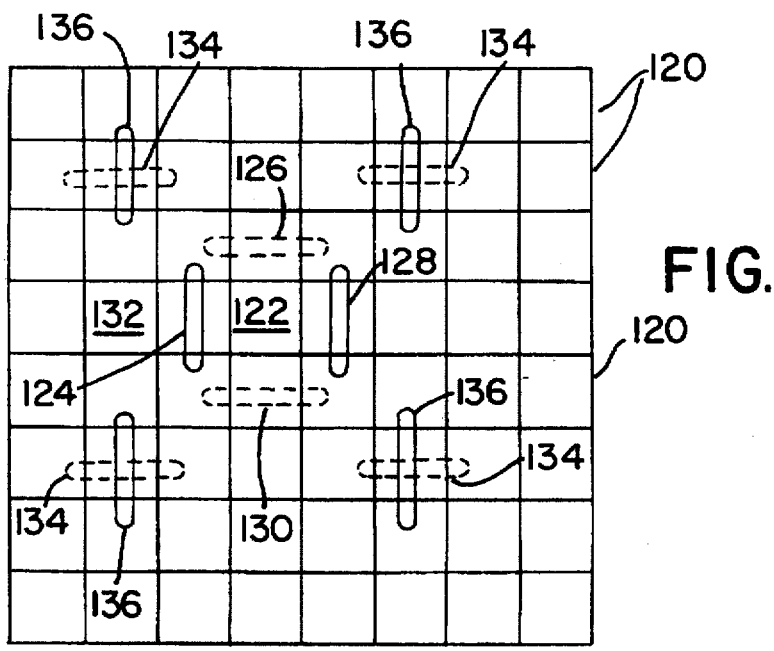
FIG. 16 is a schematic plan view of a series of non-moving thermal patterns for performing the nondestructive evaluation technique of this invention.

FIG. 16 shows a grid of selected regions 120 on a structure in which each region 120 is to be evaluated for cracks. A particular region 122 can be evaluated by four steps of heating by four distinct heating patterns: a first pattern 124 to the left of the region 122, followed by a second pattern 126 above the region 122, a third pattern 128 to the right, and a fourth pattern 130 below the region 120. In practice if discrete non-moving patterns are used, heating from the left, top, right, and bottom in that order may minimize residual gradient between successive images used to generate the crack evaluation image. It is also evident that the pattern 124 when heating the left of the selected region 122 also heats the right of a region 132. Thus to examine an entire region of a structure an array of four or more discrete heating patterns 134 may be stepped by discrete increments over the structure's surface. A single pattern in the shape of a square or circle might be sufficient. FIG. 16 shows the use of two arrays one utilizing horizontal patterns 134 and one utilizing vertical patterns 136.

Figure 4:
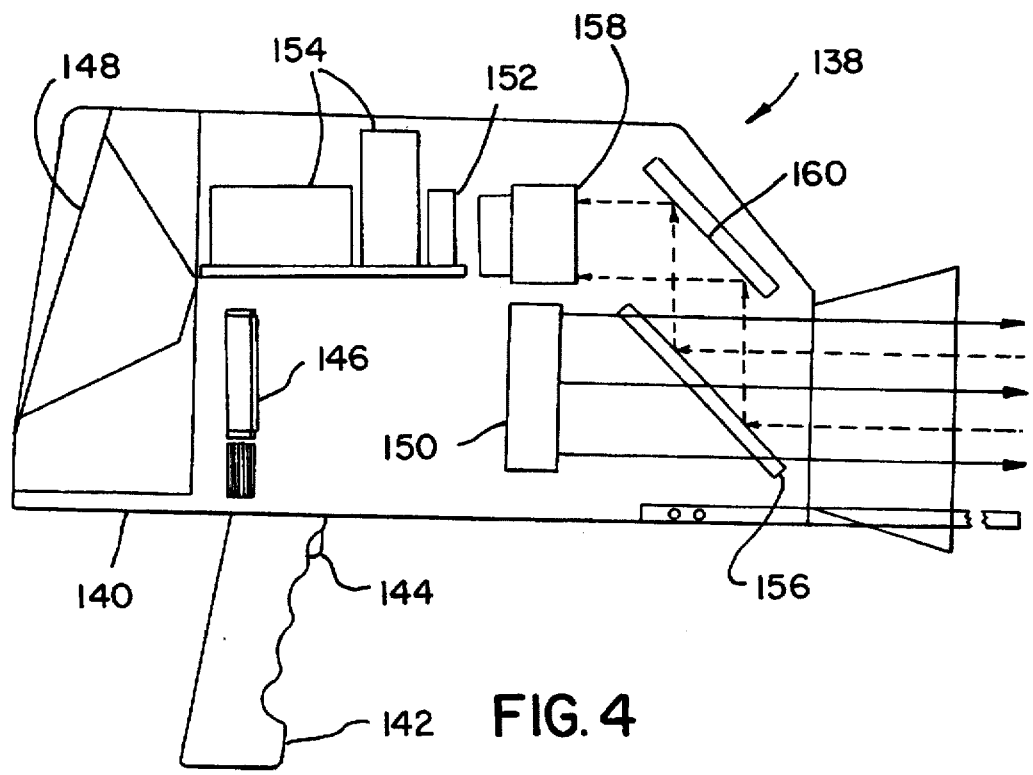
FIG. 4 is a side elevational view of another apparatus for performing the nondestructive evaluation of this invention.

To facilitate field use of the method of detecting cracks disclosed herein a handheld integrated unit 138, as shown in FIG. 4, may be employed. The unit 138 consists of a body 140 with a handle 142 which incorporates an on switch 144. The switch 144 controls the high power element such as the infrared source 146 and the display screen 148. The unit 138 incorporates both a heat source 146, an infrared projecting lens 150 with an infrared camera 152, and processing electronics 154.

When the switch 144 is actuated individual Nicrome wire are heated in the heat source 146 and are projected by the projection lens through a beam-combinor/color-separator 156 onto a bridge structure. The infrared camera 152 utilizes an infrared lens 158 and a gold infrared mirror 160 in combination with the beam-combinor/color-separator 156 to view portions of the structure in which thermal gradients are being induced by the projected infrared source 146. The combinor/color-separator 156 separates the 3-5 Micron radiation used by the infrared camera 152 from the visible and near-visible infrared radiation projected by the heat source 146. The beam-combined/color-separate 156 could also incorporate an electronic shutter and the camera 152 could be controlled to only view the structure when the shutter is closed.

It should be understood that heat flow requires a thermal gradient within a material or structure. Conversely, a thermal gradient implies a flow of heat, the rate of heat flow being governed by the slope of the gradient and the conductivity of the material in which the heat is flowing. The low conductivity of a stress crack impedes the flow of heat through a structure. Conductivity is indirectly measured by the induced gradient. A large gradient is required to cause heat flow across the stress crack. Thus the crack causes heat to build up behind the crack until the gradient across the crack is sufficient to cause heat to flow across or around the crack. Differentiation of the gradient reveals abrupt changes in conductivity which can be distinguished from abrupt changes in emissivity (such as caused by a paint chip) by the change in sign of the gradient when the direction of heat flow is changed. Changing the direction of the induced gradient changes the sign of the gradient across the crack because the direction of heat flow is reversed. Abrupt changes in emissivity cause apparent gradients which do not change sign because they are not the result of heat flow.

It should be understood that a thermal gradient feature as defined herein is a portion of a structure undergoing nondestructive evaluation which produces a nonlinear apparent change in the temperature gradient in a material. Thermal gradient features are produced by changes in surface emissivity which in turn can be caused by paint chips which have fallen away from or adhere to a surface. Changes in emissivity can also be caused by paint drips and surface contamination. Thermal gradient features can also be caused by thermal breaks in the structure of the material undergoing nondestructive evaluation. Such thermal breaks are caused by subsurface features such as stress cracks, material inclusions and material voids. The process described and claimed herein provides a means for differentiating thermal gradient features caused by changes in emissivity from thermal breaks in the structure which are indicative of material flaws.

It is understood that the invention is not limited to the particular construction and arrangement of parts herein illustrated and described, but embraces such modified forms thereof as come within the scope of the following claims.

I claim:

1. A method for finding flaws in a structure comprising the steps of:
    a) selecting a region on the structure to be examined;
    b) inducing a first flow of heat through the selected region;
    c) imaging the selected region to form at least a first thermal image after the first flow of heat has induced a first thermal gradient;
    d) inducing a second flow of heat through the selected region, wherein the second flow of heat is from a substantially different direction than the first flow of heat;
    e) imaging the selected region to form at least a second thermal image after the second flow of heat has induced a second thermal gradient; and
    f) processing the first thermal image and the second thermal image to detect thermal gradient features common to both images where the sign of the thermal gradient of the feature changes between the first thermal image and the second thermal image.

2. The method of claim 1 further comprising the step of displaying an image of the selected region which highlights the detected features common to both images where the sign of the induced gradient changes between the first thermal image and the second thermal image.

3. The method of claim 1 wherein the second induced heat flow is substantially opposite in direction from the first induced heat flow.

4. The method of claim 1 wherein the step of processing the first thermal image and the second thermal image includes the step of differentiating the first thermal image and the second thermal image to form first and second differentiated images, and subtracting the first and the second differentiated images to highlight features which change sign between the first and second images.

5. The method of claim 4 wherein the first thermal image is composed of first pixels and the second thermal image is composed of second pixels, and wherein after the step of differentiating the first thermal image and the second thermal image to form the first and second differentiated images, each first and second differentiated image having pixels corresponding to the pixels of the first thermal image and the second thermal image, further comprising the steps of: normalizing each pixel of the first differentiated image by a total corrected flux of each pixel in the first thermal image; and normalizing each pixel of the second differentiated image by a total corrected flux of each pixel in the second thermal image before the step of subtracting the first and second differentiated images to highlight features which change sign between the first thermal image and the second thermal image.

6. The method of claim 4 wherein the first thermal image and the second thermal image are differentiated digitally.

7. The method of claim 4 wherein the first and second differentiated images are measured directly with an oscillating optical system.

8. The method of claim 1 wherein the first flow of heat is caused by a thermal pattern which is projected on to the structure.

9. The method of claim 1 wherein the first flow of heat is caused by heating elements in close proximity to the structure.

10. The method of claim 1 wherein the first flow of heat is caused by heating elements in contact with the structure.

11. The method of claim 1 wherein a heating element is moved across the structure and the selected region and images of the selected region are taken before and after the heating element is moved across the selected region.

12. The method of claim 1 wherein the selected region has left, right, top and bottom sides and a pattern of infrared heat is projected on to the structure adjacent to the sides but not within the selected region.

13. The method of claim 1 wherein a first reference image is taken before inducing the first flow of heat through the selected region and the first reference image is subtracted from the first thermal image and, wherein a second reference image is taken before inducing the second flow of heat through the selecting region and the second reference image is subtracted from the second thermal image.

14. The method of claim 1 wherein the imaging of the selected region is with a camera.

15. The method of claim 14 wherein projected radiation is prevented from reflecting back to the camera by a spectral filter means.

16. The method of claim 14 wherein projected radiation is prevented from reflecting back to the camera by means of a timing shutter.

17. A thermal projection and imaging apparatus for detecting cracks in a structure, the apparatus comprising:
   a) an infrared optical element;
   b) a multiplicity of selectably energizable elements arrayed in spaced parallel relation and positioned facing the infrared optical element and positioned with respect to the optical element to focus an image of the elements on the structure; and
   c) an infrared camera focused on the image of the elements on the structure.

18. The apparatus of claim 17 wherein the infrared optical element is a reflective spherical minor having a center of curvature, and wherein the selectably energizable elements are positioned between the spherical mirror and the center of curvature of the mirror.

19. A method for performing nondestructive evaluation by observing the effects of induced heat flow in a material, wherein the material has a surface of varying emittance, the method comprising the steps of:
   a) imaging a selected region of a material to form at least a first thermal image of a first flow of heat which has a positive thermal gradient;
   b) imaging the selected region of the material to form a second thermal image of a second flow of heat which has a negative thermal gradient; and
   c) processing the first thermal image and the second thermal images to detect thermal gradient features common to both images which change sign between the first thermal image and the second thermal image.

20. An apparatus for performing nondestructive evaluation by observing the effects of induced heat flow in a structure wherein the structure has a surface of varying emittance, the apparatus comprising:
   a) a means for inducing a flow of heat in at least a first and a second directions through a selected region of a structure;
   b) a means for imaging a selected region of the structure to form at least a first thermal image of the flow of heat in the first direction which has a positive thermal gradient;
   c) the means for imaging also forming a means for imaging the selected region of the structure to form a second thermal image of the flow of heat in the second direction which has a negative thermal gradient; and
   d) a processor which processes the first thermal image and the second thermal image to detect thermal gradient features common to both images which change sign between the first thermal image and the second thermal image.

* * * * *